though I do not mean to be limited thereby, that bromide or iodide substituted catalyst intermediates are more active than aluminum chloride promoted rhodium or iridium catalysts.

United States Patent [19]

Burke

[11] Patent Number: 5,414,115
[45] Date of Patent: * May 9, 1995

[54] ISOMERIZATION OF CARBOXYLIC ACIDS

[75] Inventor: Patrick M. Burke, Wilmington, Del.

[73] Assignee: E. I. Du Pont de Nemours and Company, Wilmington, Del.

[*] Notice: The portion of the term of this patent subsequent to Jul. 3, 2007 has been disclaimed.

[21] Appl. No.: 108,416

[22] Filed: Aug. 19, 1993

[51] Int. Cl.⁶ .......................................... C07C 51/353
[52] U.S. Cl. .................................................. 562/591
[58] Field of Search ........................................ 562/591

[56] References Cited

U.S. PATENT DOCUMENTS 4,939,298  7/1990  Burke .................................. 562/591
5,166,421  11/1992 Bruner ................................ 562/522

Primary Examiner—José G. Dees
Assistant Examiner—Joseph M. Conrad, III

[57] ABSTRACT

An improved process for the isomerization of saturated alkyl carboxylic acids is obtained by using aluminum iodide or aluminum bromide promoted rhodium or iridium catalysts.

3 Claims, No Drawings

ISOMERIZATION OF CARBOXYLIC ACIDS

FIELD OF THE INVENTION

This invention relates to an improved process for the isomerization of (interconversion) of linear and branched carboxylic acid.

BACKGROUND OF THE INVENTION

Burke U.S. Pat. No. 4,939,298 discloses the isomerization of saturated alkyl carboxylic acids having 4 to 20 carbon atoms and having at least one hydrogen on a beta carbon atom by heating the acids in a solvent in the presence of a rhodium catalyst promoted with an iodide or bromide and carbon monoxide.

SUMMARY OF THE INVENTION

The present invention is an improvement and expansion of the subject matter of the '298 patent. The presence of aluminum in the reaction mixture results in a higher isomerization rate, and greater catalyst stability. The '289 patent discloses rhodium as the catalytic metal, and it has now been found that iridium in conjunction with an aluminum compound is also a satisfactory catalytic metal for this reaction.

The present invention is a process for the isomerization of saturated alkyl carboxylic acids having 4 to 20 carbon atoms and having at least one hydrogen on a beta carbon atom, which comprises heating a reaction medium containing said saturated acid, a solvent for said saturated acid, an aluminum iodide or aluminum bromide promoted rhodium or iridium catalyst, and carbon monoxide to a temperature in the range of 170 to 250 degrees C. at a carbon monoxide pressure of 200 to 10,000 psi, where the amount of iodide or bromide promoted rhodium or iridium catalyst is in the range of 0.005 to 0.50% by weight of rhodium or iridium metal based on the weight of the reaction medium. The conversion may be from a branched compound to a linear compound, or from a linear compound to a branched compound, or from a branched compound to an isomeric branched compound.

The rhodium or iridium catalyst may be formed in-situ by adding a rhodium compound or a iridium compound and a suitable aluminum iodide compound or aluminum bromide compound to the other components of the mixture to be reacted. Alternatively, aluminum and iodide or bromide may be added separately to the mixture, or the promoted catalyst may be prepared prior to addition to the mixture. The aluminum iodide or bromide may also be formed in-situ from suitable aluminum and iodide precursors. Aluminum tri-iodide is the preferred promoter.

The isomerization may be carried out in a solvent for the compound being isomerized. Lower aliphatic acids are suitable, and acetic acid is satisfactory. Other solvents are aliphatic halides such a methylene chloride, aromatic solvents such as toluene and xylene, and polar aprotic solvents such a tetramethylene sulfone.

DETAILED DESCRIPTION OF THE INVENTION

The carboxylic acid must have at least one hydrogen on a beta carbon atom. The beta carbon atom is the one marked with the asterisk in the formula

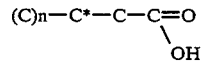

where n is 0 to 17

A particularly preferred process involves the isomerization of C6 acids to adipic acid, for example the isomerization of 2-methylglutaric acid or ethylsuccinic acid. The isomerization reaction can be just the reverse of the above, i.e. the conversion of adipic acid into 2-methylglutaric acid.

The rhodium or iridium component of the catalyst can be made from any suitable rhodium or iridium compound, for example any complex that is free from interfering ligands, such as bidentate phosphine and nitrogen ligands. Among the materials which can be employed as the source of the iridium are iridium metal, iridium salts, iridium oxides, iridium carbonyl compounds, organoiridium compounds, coordination compounds of iridium and mixtures thereof. Specific examples of such compounds include, but are not limited to, iridium(III) chloride and its hydrates, iridium(III) bromide and its hydrates, iridium(III) iodide, iridium(III) oxide, iridium(IV) oxide, iridium(III) acetylacetonate, iridium(I) dicarbonyl acetylacetonate, iridium (III) nitrate, iridium(III) ethylhexanoate and iridium metal. Preferred sources of iridium catalyst include iridium(III) chloride and its hydrates, iridium(III) iodide, and iridium(I) dicarbonyl acetylacetonate. The analogous rhodium compounds may be used to prepare rhodium based catalysts. The Burke '298 patent at column 2 lines 20 through 35 lists other suitable rhodium compounds.

The concentration of promoted catalyst is not critical but is usually maintained in the range of about 0.005 to 0.50% by weight of rhodium or iridium based upon the weight of the reaction medium. Stated in terms of the amount of rhodium or iridium employed per amount of compound to isomerized, the ratio of 1 part by weight of catalyst metal to 50 to 200 parts by lo weight of the compound to be isomerized is satisfactory. Aluminum iodide and aluminum bromide are preferred promoters. Generally the concentration of the iodide or bromide is between 0.05 and 4.5 % by weight based upon the weight of the reaction medium and at a mole ratio to catalyst metal (rhodium or iridium) in the range of 1/1 to 15/1 preferably 2/1 to 6/1. In order to obtain the benefits of the present invention, aluminum should be in the reaction mixture in a molar ratio of aluminum to iodide or bromide of about 1/5 to 2/1. Often the aluminum is added as aluminum trihalide and the rhodium or iridium is added as a halide-free carbonyl derivative in which case the molar ratio of aluminum to halide is of course 1/3.

Water may be produced during the course of the reaction. The water concentration should normally be less than 3% and preferably in the range of 0.0 to 1.0%

When the catalytic metal is rhodium, the usual temperature range of operation is about 200 to 250 degrees C., and preferably about 220 to 230 degrees C. When the catalytic metal is iridium, the usual temperature range of operation is about 200 to about 230 degrees C. and preferably in the range of about 210 to 220 degrees C.

The usual carbon monoxide partial pressure is in the range of about 100 to 3000 psi and preferably about 200 to 1500 psi. The optimum carbon monoxide partial pressure will depend on temperature, catalytic metal and solvent.

EXAMPLES

Example 1

A 160 ml mechanically stirred zirconium autoclave was flushed with nitrogen and then with 50 psi carbon monoxide. It was then charged with a solution of 7.3 grams (50) mmole of 2-methylglutaric acid(MGA), 91.7 grams of acetic acid, 0.32 gram (0.78 mmoles) of aluminum tri-iodide, 0.5 gram (84 mmoles) water and 0.20 gram (0.78 mmole) rhodium dicarbonyl acetylacetonate. The iodide to rhodium molar ratio was 3:1.

The autoclave was pressured with carbon monoxide to 300 psi, heated to 220 degrees C. and the pressure was immediately adjusted with carbon monoxide to 700 psi at 220 degrees C. Carbon monoxide was continuously fed to the autoclave so as to maintain the total pressure constant at about 700 psi. Samples were removed at intervals for analysis. The reaction was allowed to run for a total of 4 hours after which it was cooled to 20 degrees C. The excess carbon monoxide was vented and the product recovered.

Samples were esterified with BF3/methanol and analyzed as their methyl esters on a GC column and the results are shown in Table 1.

Control Example 1

Example 1 was repeated except that the Aluminum tri-iodide was replaced with an equivalent amount of hydrogen iodide as a 57% aqueous solution (0.53 gram). The results are shown in Table 1.

Example 2

Example 1 was repeated except that the temperature was reduced to 210 degrees C and the rhodium catalyst was replaced with an equivalent amount of iridium as iridium dicarbonly acetylacetonate (0.32 gram; 0.78 mmole). The results are shown in Table 1.

Control Example 2

Example 2 was repeated except that the aluminum tri-iodide was replaced with an equivalent amount of hydrogen iodide as a 57% aqueous solution (0.53 gram). The results are shown in table 1.

TABLE 1

| Example | MGA Conversion % 2 hrs. | MGA Conversion % 4 hrs. | Yield Index* at 10% Conversion |
|---|---|---|---|
| 1 | 35.0 | 49.7 | 89.8 |
| control 1 | 20.7 | 30.2 | 88.8 |
| 2 | 16.5 | 43.6 | 65.3 |
| control 2 | 10.7 | 20.9 | 70.1 |

*Yield Index = AA/(AA + VA + MBA)
VA = mole % Valeric acid
MBA = mole % Methylburfic acid
AA = mole % Adipic acid Conclusion:

Isomerization was more rapid with aluminum iodide promoted rhodium and iridium catalysts than with hydrogen iodide promoted rhodium and iridium catalysts. The adipic acid yield, as measured by Yield Index at 10% conversion was about the same for both aluminum iodide and hydrogen iodide promoted catalysts.

Example 3

A 160 ml mechanically stirred zirconium autoclave was flushed with nitrogen and then with 50 psi carbon monoxide. It was then charged with a solution of 7.3 grams (50 mmole) of 2-methylglutaric acid (MGA), 1.0 gram dl-2,3-dimethylsuccinic acid, 88.0 grams of acetic acid, 0.32 gram (0.78 mmole) of aluminum tri-iodide, 1.6 grams water and 2.1 grams (0.58 mmole) rhodium carbonyl di-iodide in acetic acid-water (3:2). The total iodide to rhodium ratio was 6:1.

The autoclave was pressured with carbon monoxide to 500 psi, heated to 230 degrees C. and the pressure was immediately adjusted with carbon monoxide to 1000 psi at 230 degrees C. Carbon monoxide was continuously fed to the autoclave so as to maintain the total pressure constant at about 1000 psi. Samples were removed at intervals and analyzed for rhodium and conversion. The reaction was allowed to run for a total of 20 hours after which it was cooled to 20 degrees C. The excess carbon monoxide was vented and the product was recovered.

The samples from the reactor were analyzed by GC as methyl esters and by X-ray fluorescence for rhodium in solution (as a percentage of original rhodium concentration). The results are shown in Table 2.

Control Example 3A

Example 3 was repeated except that the aluminum iodide was omitted. The results are shown in table 2.

Control Example 3B

Example 3 was repeated except that the aluminum iodide was replaced with an equivalent amount of 2-iodobutane and the total initial water concentration was 1%. The results are shown in Table 2.

TABLE 2

| Example | I/Rh ratio | % Rh in solution (after 20 hours) | MGA Conv. (4 hrs) | Yield Index (4 hrs) |
|---|---|---|---|---|
| 3 | 6 | 79 | 52.8 | 60 |
| 3A | 2 | 52 | 15 | 88.1 |
| 3B | 6 | 44 | 53.8 | 54.4 |

Conclusion:

The amount of rhodium remaining in solution is much higher when aluminum iodide is present and the activity of the catalyst for isomerization is also greatly increased. When an organic iodide is used as the iodide source the catalyst activity is about the same as when aluminum is present, but more of the catalyst precipitates from the solution.

Example 4

(Rhodium + 2-iodobutate Promoter + 2 Equivalents Aluminum Isopropoxide)

Rhodium/Aluminum Isopropoxide Catalyzed Isomerization of Methylglutaric acid to Adipic acid in Acetic acid at 220 C/700 psi.

A 160 ml mechanically stirred zirconium autoclave was flushed with nitrogen and then with 50 psi of carbon monoxide. It was then charged with a solution of 7.3 grams (50 mmole) of 2-methylglutaric acid (MGA), 91.4 g of acetic acid, 0.32 g (1.56 mmoles) of aluminum isopropoxide, 0.8 g (4.68 mmoles) 2-iodopropane and 0.20 g (0.78 mmole) rhodium dicarbonyl acetylacetonate. The iodide to rhodium ratio was 6:1. The autoclave was pressured with carbon monoxide to 300 psi, heated to 220 C. and the pressure was immediately adjusted with CO to 700 psi at 220 C. Carbon monoxide was continuously fed to the autoclave from a reservoir so as to maintain the total pressure constant at about 700 psi. Samples were removed at intervals for GC analysis. The reaction was allowed to run for a total of 2 hours after which it was cooled to 20 C. The excess CO was vented through a control valve and the product was discharged. The samples from the reactor were esterified with BF3/Methanol and analyzed as their methyl esters on a 30 m Carbowax capillary GC column. The results are shown in Table 3.

Control Example 4A (Rhodium+2-iodobutane Promoter)

Rhodium/2-iodopropane Catalyzed Isomerization of Methylglutaric acid to Adipic acid in Acetic acid at 220 C.

The experiment in Example 4 was repeated except that the aluminum isopropoxide was omitted. The results are shown in Table 3.

Comparative Example 5 (Rhodium +2 equivalents of Aluminum iodide)

Rhodium/Aluminum Iodide Catalyzed Isomerization of Methylglutaric acid to Adipic acid in acetic acid at 220 C.

The experiment in Example 4 was repeated except that the aluminum isopropoxide was replaced with an equivalent of aluminum iodide (0.64 g; 1.56 mmoles) and the 2-iodopropane was omitted. The results are shown in Table 3.

TABLE 3

| Example | Aluminum Compound | I/Rh | MGA Conv (4 hrs) | Yield Index (4 hrs) |
|---|---|---|---|---|
| 4 | Al(i-OPr)3 | 6 | 40.0 | 87.7 |
| 4A | None | 6 | 16.2 | 86.6 |
| 5 | AlI3 | 6 | 40.0 | 86.2 |

The results indicate that addition of aluminum isopropoxide greatly accelerates the rate of isomerization of MGA and that alumiuun isopropoxide in conjunction with an alkyl iodide is equivalent in activity to aluminum iodide at the same iodide to rhodium ratio.

I claim:

1. A process for the isomerization of saturated alkyl carboxylic acids having 4 to 20 carbons atoms and having at least one hydrogen on a beta carbon atom, which comprises heating a reaction medium containing said saturated acid, a solvent for said saturated acid, an aluminum iodide or aluminum bromide promoted rhodium or iridium catalyst, and carbon monoxide to a temperature in the range of 170 to 250 degrees C. at a carbon monoxide pressure of 200 to 10,000 psi, where the amount of iodide or bromide promoted rhodium or iridium catalyst is in the range of 0,005 to 0.50% by weight of rhodium or iridium metal based on the weight of the reaction medium, and the mole ratio of iodide or bromide to rhodium or iridium is 1/1 to 15/1 and the mole ratio of aluminum to iodide or bromide is 1/5 to 2/1.

2. The process of claim 1 in which the aluminum component of the aluminum iodide or aluminum bromide promoted rhodium or iridium catalyst is added in a form other than aluminum iodide or aluminum bromide.

3. The process of claim 1 in which the saturated acid is 2methylglutaric acid and said acid is isomerized to adipic acid.

* * * * *